United States Patent
Vanaja et al.

(10) Patent No.: US 7,790,112 B2
(45) Date of Patent: Sep. 7, 2010

(54) BIOSENSOR TO DETERMINE POTASSIUM CONCENTRATION IN HUMAN BLOOD SERUM

(75) Inventors: Sunkam Vanaja, Andhra Pradesh (IN); Mandapati Jayalakshmi, Andhra Pradesh (IN); Sunkara Sakunthala Madhavendra, Andhra Pradesh (IN); Kaki Rajgopal, Andhra Pradesh (IN); Mannepalli Lakshmi Kantam, Andhra Pradesh (IN); Sunkara Vardhireddy Manorama, Andhra Pradesh (IN); Vinod Kumar Khanna, Rajasthan (IN); Shamim Ahmad, Rajasthan (IN); Yogendra Kumar Jain, Rajasthan (IN); Chandra Shekhar, Rajasthan (IN)

(73) Assignee: Council of Scientific & Industual Research (IN)

( * ) Notice: Subject to any disclaimer, the term of this patent is extended or adjusted under 35 U.S.C. 154(b) by 230 days.

(21) Appl. No.: 11/691,712

(22) Filed: Mar. 27, 2007

(65) Prior Publication Data

US 2007/0227886 A1 Oct. 4, 2007

(30) Foreign Application Priority Data

Mar. 30, 2006 (IN) .......................... 898/DEL/2006

(51) Int. Cl.
*G01N 27/26* (2006.01)
(52) U.S. Cl. ................... 422/82.03; 436/74; 436/79; 204/413; 204/403.01
(58) Field of Classification Search ............. 436/74, 436/79; 540/468, 469, 472; 204/413; 422/82.03
See application file for complete search history.

(56) References Cited

U.S. PATENT DOCUMENTS

| | | | | |
|---|---|---|---|---|
| 4,352,726 A | * | 10/1982 | Sugano et al. | 204/413 |
| 4,844,097 A | | 7/1989 | Bellhouse et al. | |
| 5,136,033 A | * | 8/1992 | Masilamani et al. | 540/468 |
| 5,250,168 A | | 10/1993 | Tsukada et al. | |
| 6,962,992 B2 | | 11/2005 | Martin et al. | |

FOREIGN PATENT DOCUMENTS

EP 0125555 A2 11/1984
JP 61254844 11/1986

OTHER PUBLICATIONS

A New Electrode Consisting of Prussian Blue/Dibenzo-18-Crown-6 Ion Pair complex for Electrochemical Capacitor Applications M. Jayalakshmi, P. Radhika, M. Mohan Rao Journal of Power Sources Nov. 14, 2005.*

* cited by examiner

*Primary Examiner*—Jill Warden
*Assistant Examiner*—Dwan A Gerido
(74) *Attorney, Agent, or Firm*—Luedeka, Neely & Graham, P.C.

(57) ABSTRACT

The present invention relates to the development of a biosensor to determine potassium in human blood serum using dibenzo-18-crown-6 (DB18C6) as ionophore. Human blood serum contains potassium in ppm levels i.e 137 to 200 mg/litre and sodium co exists with a 30 times higher concentration. Such a high concentration tends to interfere the selectivity towards potassium, but DB18C6 proves to have an excellent selectivity towards potassium and is highly sensitive to the lowest concentration of potassium levels present in the human blood serum. So the present invention reports the fabrication and characterization of ISFET (Ion Selective Field Effect transistor) coated with a monolayer of crown ether, dissolved in chloroform, on the gate of electrode.

13 Claims, 10 Drawing Sheets

Binding of the K$^+$ ion within the crown ether molecular structure (Host-guest interaction).

Fig. 1 Binding of the K⁺ ion within the crown ether molecular structure (Host-guest interaction).

Fig. 2. Schematic cross-section of potassium ISFET.

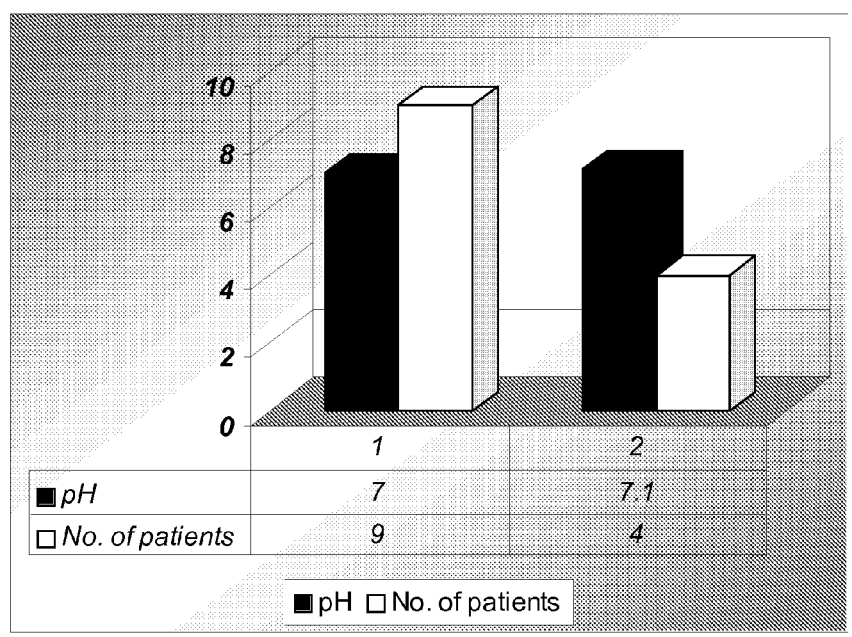
Fig.5 Study of pH distribution of blood serum samples.

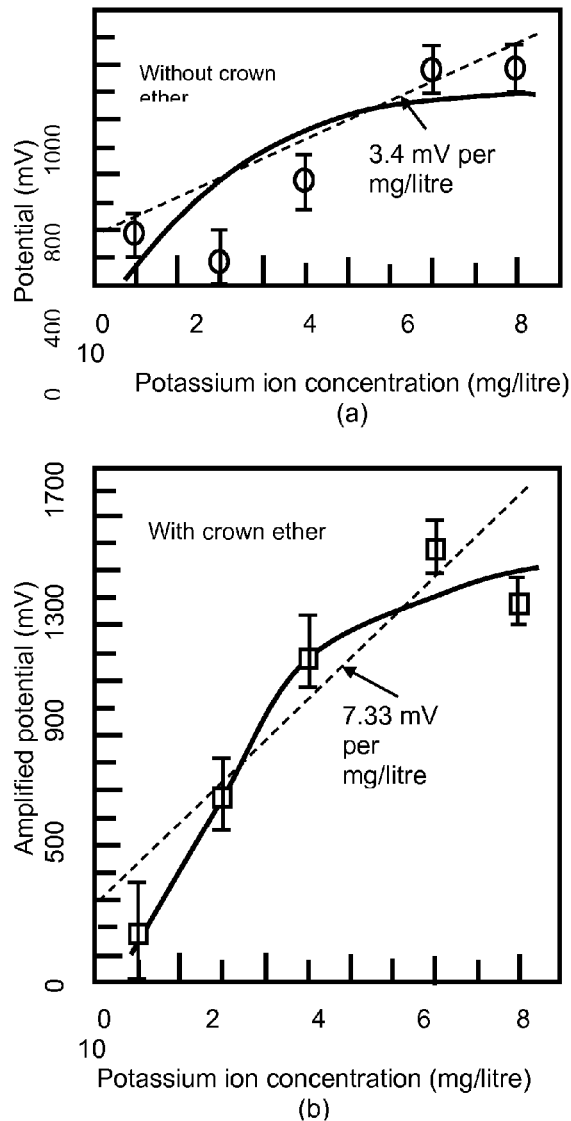
Fig. 6 ISFET response characteristics at very low KCl concentrations (a) without and (b) with crown ether layer on the gate.

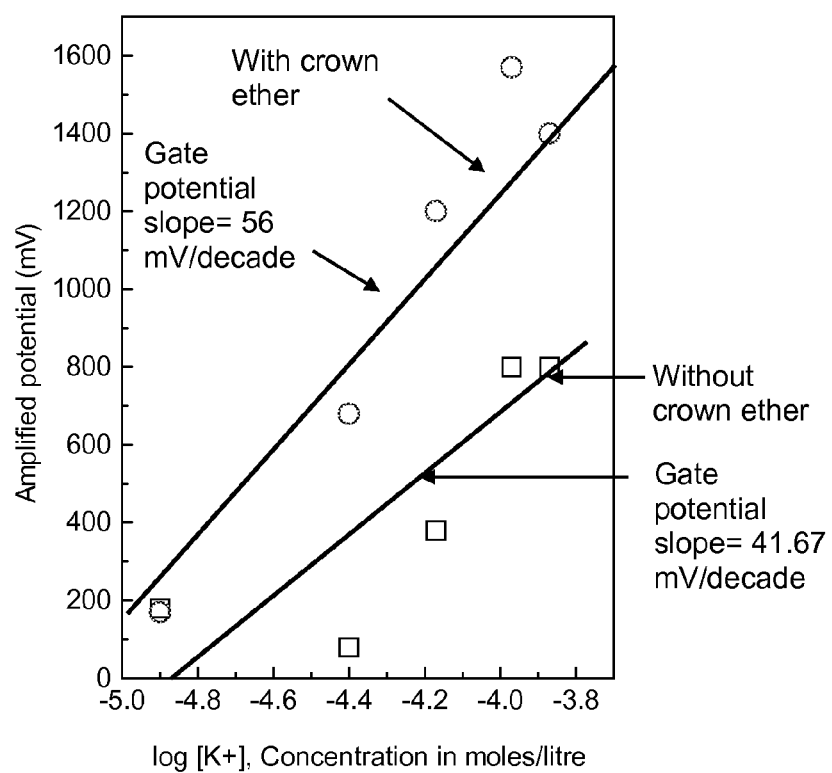
Fig.7 Semi-logarithmic plots for the ISFET characteristics of Fig.6.

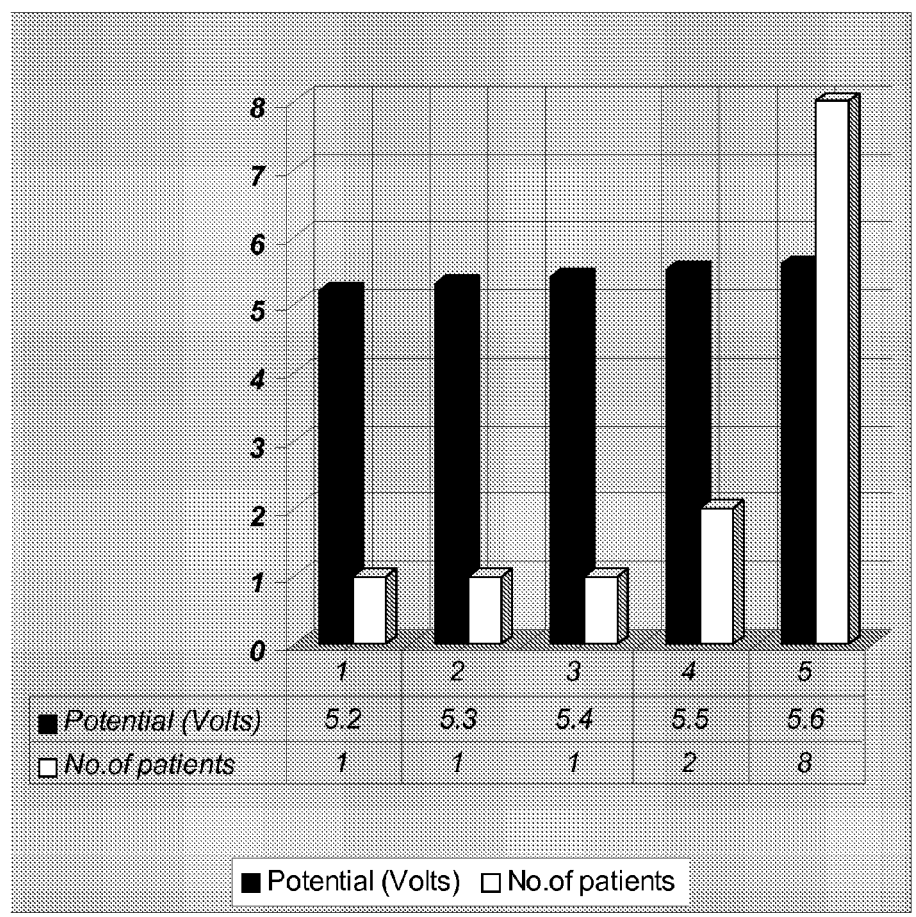
Fig. 8 Distribution of ISFET potential with number of patients.

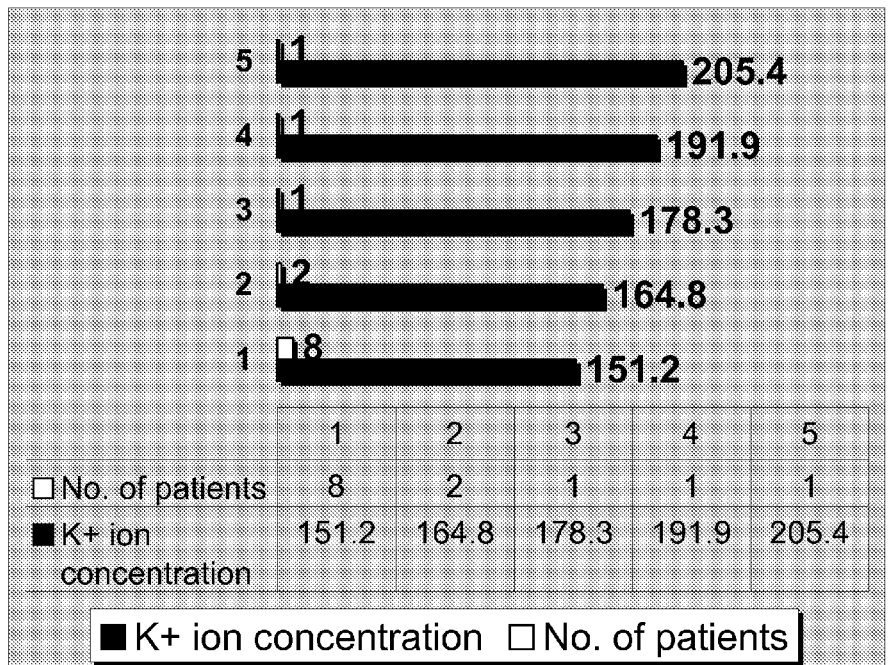

Fig. 9 Distribution of potassium ion concentration with the number of patients. The distribution has been determined by placing the maximum frequency of occurrence of ISFET output potential at the mean potassium ion concentration (151.25 mg/litre) and calculating the remaining points from their deviation about this mean value and the ISFET sensitivity for potassium.

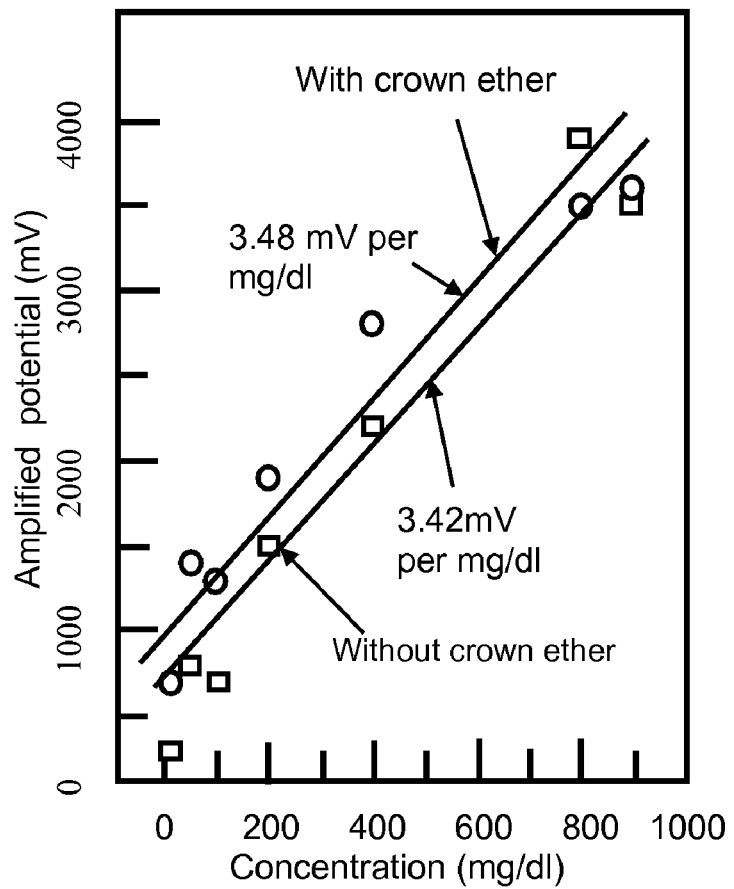
Fig. 10 Plots of potential versus NaCl concentration for ISFETs, without and with crown ether layer on the gate.

BIOSENSOR TO DETERMINE POTASSIUM CONCENTRATION IN HUMAN BLOOD SERUM

FIELD OF INVENTION

The present invention relates to the development of a biosensor to determine potassium in human blood serum using dibenzo-18-crown-6 (DB18C6) as ionophore. This invention also reports the fabrication and characterization of ISFET (ion-sensitive field-effect transistor) coated with a monolayer of crown ether on the gate of the electrode. D18C6 dissolves in chloroform and tends to form a monolayer on the surface of working electrode. Human blood serum contains potassium in ppm levels i.e. 137 to 200 mg/litre and sodium co-exists with a 30 times higher concentration. Such a high concentration tends to interfere the selectivity of potassium but D18C6 proves to have an excellent selectivity towards potassium and is highly sensitive to the lowest concentration of potassium levels present in the human blood serum.

Total absence or very low chemical interaction between materials constituting a sensor and a biological sample of human electrolytes is very important in both, chronic illness and in acute menacing conditions. Potentiometric methods based on ion-selective electrodes serve this purpose far better than optical methods in clinical laboratories. This potentiometric based potassium biosensor is easy to prepare, assemble, economically viable. It could be used in the disposable mode if it is made in the form of strip that has the dimensions of the ISFET gate. The chances to marketability are very high as the preparative method does not involve complicated procedure and is economically very promising because each fresh monolayer requires less than 500 microgram of the crown ether. The response time of ionophore was within a minute and the shelf life of the electrode either on use or idle, was found to be a three months period. The electrode surface can be re-coated and used.

BACKGROUND AND PRIOR ART OF THE INVENTION

Potassium monitoring in whole blood is one of the most important routine analysis performed in clinical laboratory, it is of fundamental importance both for the early detection of post-operative shock and for heart surgery. Determination of potassium contents of serum, urine, and foods is also very important in clinical and medical fields, since the potassium contents are related to renal diseases. These diseases restrict patients to a diet containing a large amount of potassium. From the potassium determination, medical information concerning physical conditions of the patient can be obtained. In the case of hypopotassemia, alkalosis, cirrhosis of liver, diuretic drugs, etc. are suspected. On the other hand, when potassium concentration in human serum becomes higher than 9 mmol dm$^{-3}$, heart often stops.

Biological active-transport systems involving ions, in particular K$^+$, have important functions in the organism, which are essential for regulation of many intracellular activities. These systems are related in the transmission of information by the nervous system and in the excitation and relaxation cycle of muscle tissue. Principally, accurate, easy and rapid sensing of potassium ions in human blood serum is very important prior to cardiac surgery to assess the condition of the patient.

Crown ethers have been reported to be an inexpensive neutral carrier in the construction of Ion Selective Field Effect Transistors. Additionally, these carriers have the option of covalently attaching the desired molecule for electro analytical applications. The characteristic of crown ether is their selective complexation ability. They bind the cationic portion of alkali and alkaline earth metal salts (guest) in to the cavity of the crown ring (host). The selectivity is dependent principally on the relative size of the cavity of the crown ring and the diameter of the cation, number of donor atoms in the crown ring and the topological effect and the relationship between the hardness of the cation and that of the donor atom, and charge number of the cation. In the case of crown complexes, a metal cation-anion contact always occurs from the open faces of the ring plane. Dibenzo-18-crown-6 used here was shown to have a circular cavity of diameter 2.6-3.2 A° which fits the exact size of potassium ion of 2.66 A° and makes it an excellent choice to be a sensing material for potassium ions.

Potentiometry using ion selective electrodes (ISE) is the method of choice due to the easy and fast performance of the assay. About 200 million clinical assays of potassium every year are performed using ISEs in the USA. It is well-known that ion selective electrodes are based on the use of a water-insoluble membrane that can be considered as a water-immiscible liquid of high viscosity, containing an ionophore which binds selectively the ion of interest and it generates a membrane potential. Potentiometric detection based on ion-selective electrodes, as a simple method, offers several advantages such as speed and ease of preparation and procedures, simple instrumentation, relatively fast response, wide dynamic range, reasonable selectivity and low cost. Besides, they are ideally suitable for on-site analysis and, nowadays, were found to be applicable in the analysis of some biologically relevant ions, process control and environmental analysis. Miniaturization of the system is realized using silicon technology. The potassium concentration is measured potentiometrically using ISFET coated with crown ether in combination with an Ag/AgCl reference electrode integrated on the same chip. To overcome problems resulting from a long time contact of the sensor with protein-containing sample solution, an automated measuring protocol was applied where the sensor is brought in contact with the sample only for short time segments. Immediately after the stabilization of the measuring signal the chip is flushed with a commercial Ringer solution of constant potassium concentration. The frequency of sample/conditioning solution cycles depend on the diagnostic demand. In this way the active sensing area of the sensor is cleaned time to time from the sample. Furthermore, the sensor signal in the cleaning solution serves as a calibration point.

Potentiometric ion sensors based on ion-sensitive field-effect transistors (ISFETs) are attracting increasing attention primarily because of their small size, robustness, low cost, fast response time and low output impedance. For the ISFET, the metal connection of the reference electrode acts as a remote gate. The equation giving the dependence of threshold voltage on the pH of the solution in contact with the gate is, $$V_{Th}(\text{ISFET}) = E_{ref} - \Phi_{si} - \psi + \chi - Q_f/C_d + 2|\phi_p| + 1/C_d\sqrt{2\epsilon_o\epsilon_s q N_A(2|\Psi_p|)} \quad (1)$$

where $E_{ref}$ is the constant reference electrode potential $\Phi_{si}$ is the silicon work function, $\chi$ is surface dipole potential of the solvent and $\Psi$ is the interfacial electrostatic potential at the solution/dielectric interface whose sensitivity to changes in bulk pH is expressed by the equation, $$\partial\Psi/\partial p^H = -2.303(RT/F)\alpha \quad (2)$$

R is universal gas constant, T is absolute temperature, F is Faraday's constant and $\alpha$ is a dimensionless sensitivity parameter ($0<\alpha<1$), given by, $$\alpha = 1/(2.303 KTC/q^2\beta) + 1 \qquad (3)$$

k is Boltzmann constant, T is temperature in Kelvin scale, C is the differential double layer capacitance at the insulator-electrolyte interface, q is electronic charge and $\beta$ is surface proton buffer capacity determining the ability of the gate dielectric surface to absorb or release protons.

But the silicon dioxide-silicon nitride gate ISFET shows sensitivity to various ions in aqueous solution such as $H^+$, $Na^+$, $K^+$, $Ca^+$, $Zn^{++}$, $Fe^{++}$, etc., besides $H^+$-ion. Extension of ISFETs for measuring species other than hydrogen ions is a vital research area. ISFETs with ion-sensitivity and selectivity to different ionic species can be fabricated by depositing polymeric membranes containing specific receptor molecules on the gate surface.

Reference to be made to a publication by Shoji Motomizu et al, Analyst, 1988, 113, 743-746 wherein potassium in river water was determined by a spectrophotometric method involving flow injection coupled with solvent extraction. Dibenzo-18-crown-6 was used along with the dichloro derivative of ethyl orange. The procedure was shown to have less interference from foreign ions and the sensitive up to a potassium ion concentration of $10^{-5}$ M. The main problem is that dye employed in this study was dissolved in lithium hydroxide and hence the pH of the reagent solution was 10 which were unsuitable to determine potassium ions in blood serum.

Reference may be made to a publication by E. Malavolti et al, Analytica Chimica Acta 1999, 401, 129-136 wherein an optrode for continuous monitoring of potassium in whole blood was realized using valinomycin as ionophore and a neutral chromoionophore whose absorbance depends on the pH of the local environment. Membrane preparation was complicated and involves the following chemicals: chromoionophore, tetrahydrofuran, valinomycin, potassium tetrakis(4-chlorophenyl)borate, bis(2-ethylhexyl) sebacate and PVC. The main drawback of this protocol is that the sensor is sensitive to pH and maintenance of the thickness of the membrane. Otherwise, as the potassium concentration changes, all the components in the membrane bulk would shift to the new equilibrium so that there will be a change in the signal.

Reference may be made to a publication by P. C Pandey and R. Prakash, Sensors and Actuators 1998, B 46, 61-65 wherein a potassium ion-selective electrode using PVC matrix membrane impregnated with dibenzo-18-crown-6 at the surface of the polyindole modified electrode is reported. The lowest detection limit for the potassium ion sensor is $7.0\times10^{-6}$ mol $dm^{-3}$. The inherent disadvantages of this work are that preparation of sensor electrode requires tedious and complicated procedure and the selectivity of potassium ion over other cations in the same solution or human blood serum is not reported. The lowest detection limit was higher than the concentration of potassium in blood serum.

Reference may be made to a publication by Albrecht Uhlig et al, Sensors and Actuators B, 1996, 34, 252-257 wherein a miniaturised ion-selective sensor chip for potassium measurement in vivo for whole blood. Here, Valinomycin was used as ionophore and the potassium concentration is measured potentiometrically using an ion selective polymer membrane in combination with an Ag/AgCl/p-HEMA reference electrode integrated on the same chip. The main problem is the clotting of blood that has to be prevented by addition of an external reagent and unacceptable drift, which might be due to the solid state internal contact, loss of membrane ingredients and water absorption.

Reference may be made to a publication by Johan Bobaka et al, Analytica Chimica Acta, 1999, 385, 195-202 wherein all-solid-state potentiometric potassium-selective electrodes with plasticizer-free membranes were prepared by incorporation of valinomycin as the ionophore and potassium tetrakis [3,5-bis(trifluoromethyl)phenyl]borate as the lipophilic additive in a semiconducting conjugated polymer matrix of poly (3-octylthiophene). The membrane components were dissolved in chloroform and deposited on glassy carbon by solution casting. The main bottleneck is the sub-Nernstian response, the degradation of the response with time, especially for thin membranes and the observation of a relatively large ion transfer resistance at the membrane/solution interface.

Reference to be made to a publication by Carlos Alexandre Borges Garcia et al, Journal of Pharmaceutical and Biomedical Analysis 2003, 31, 11-18 wherein a simple and rapid method was developed for the K+ions determination employing a flow injection system using a flow-through electrode based on the naturally-occurring antibiotic ionophore nonactin occluded in a polymeric membrane. The nonactin ionophore was trapped in poly (ethylene-co-vinyl acetate) (EVA) matrix (40% w/w in vinyl acetate) and dispersed on the surface of a graphite-epoxy tubular electrode. The plasticizer-free all-solid-state potassium-selective electrode showed a linear response for $K^+$ ion concentrations between $5.0\times10^{-5}$ and $5.0\times10^{-2}$ M with a near-Nernstian slope of 51.5 mV per decade, when Tris-HCl buffer (pH 7.0; 0.1 M) was employed as a carrier. The major setback is the maintenance of neutral pH in samples with ammonium ion as analytically interfering ion and sensing range of $K^+$ ion concentration was well above the blood serum range.

Reference to be made to a publication by N. Abramova et al, Talanta, 2000, 52, 533-538 wherein application of a potassium ion sensor based on an ion sensitive field effect transistor (ISFET) for ion control of a dialysis solution in an artificial kidney and in blood plasma of patients treated by hemodialysis is presented. Commercial potassium ionophore valinomycin is used. The studied ISFETs have the required stability and sensitivity to monitor the potassium ion concentration in dialysis solutions within the artificial kidney apparatus. The major drawback is that ISFETs have not been tried on real blood samples.

Reference to be made to a publication by Daniela P. A. Correia et al, Talanta, 2005, 67, 773-782 wherein an array of potentiometric sensors for simultaneous analysis of urea and potassium in blood serum samples were developed. Urea biosensors based on urease immobilized by crosslinking with BSA and glutaraldehyde coupled to ammonium ion-selective electrodes were included in arrays together with potassium, sodium and ammonium PVC membrane ion-selective electrodes. Coupling of biosensors with ion-selective electrodes in arrays of sensors raises a few problems related to the limited stability of response and unidirectional cross-talk of the biosensors, and this matter was also subjected to investigation in this work. Up to three identical urea biosensors were included in the arrays, and the data analysis procedure allowed the assessment of the relative performance of the sensors. The major disadvantage is lack of identical cross-talk between urea sensors with other biosensors. This arises mainly due to the irregular enzymatic layer in some biosensors as a consequence of the procedure used for enzyme immobilization.

OBJECTS OF THE INVENTION

The main object of the present invention is to develop a biosensor to determine potassium in human blood serum. Dibenzo-18-Crown-6 (DB18C6) is proven to be the ideal ionophore. ISFET (Ion sensitive field effect transistor) made of dual dielectric $SiO_2$—$Si_3N_4$ gate has a channel length L=12 microns and channel width W=4800 microns is used as the working electrode. D18C6 ionophore is deposited on the gate of ISFET. Calibrations in standard KCl solutions showed that the sensitivity of Crown Ether-ISFET towards potassium was double that of the nitride gate-ISFET. The same observation was noted for blood serum samples.

Another object of the present invention is the investigation of cross-sensitivity of sodium ions in presence of standard KCl solutions.

Still another object of the present invention is the investigation of cross-sensitivity of sodium ions in diluted human blood serum samples.

An object of the present invention, is to study the sensitivities of ISFET with/without the crown ether layer on the gate towards potassium and sodium ions in various concentration ranges Potassium: 100-400 mg/L; Sodium: 200:1000 mg/dl.

Another object of the present invention is to study the ISFET response characteristics (a) without and (b) with crown ether layer on the gate; by carrying out standardization measurements out in standard KCl solutions with concentrations in human blood serum range (FIG. 3).

Still another object of the present invention is to study the sensitivity of the ISFET with and without crown ether on the gate towards sodium ion was found to be comparatively less than that of crown ISFET for potassium, ensuring that sodium in blood serum did not interfere with the measurements. (FIG. 10)

SUMMARY OF INVENTION

Accordingly the present invention deals with the development of biosensor to direct potentiometric determination of total potassium concentration in human blood serum. The biosensor developed consists of Dibenzo-18-crown-6 as ionophore and ISFET (Ion-sensitive field effect transistor) as substrate with in-built Ag/AgCl reference electrode. Normally, the silicon dioxide-silicon nitride gate ISFET shows sensitivity to various ions in aqueous solution such as $H^+$, $Na^+$, $K^+$, $Ca^+$, $Zn^{++}$, $Fe^{++}$, etc., besides $H^+$-ion. Extension of ISFETs for measuring species other than hydrogen ions is a vital research area. ISFETs with ion-sensitivity and selectivity to different ionic species can be fabricated by depositing polymeric membranes containing specific receptor molecules on the gate surface. Earlier works employing the anthryl azacrown structures (crown-5, crown-6) have been shown to be sensitive to sodium and potassium cations among others, although the selectivity for these ions over other alkali metal ions is only modest. Hence to identify an ionophore such as dibenzo-18-crown-6 that specifically selects potassium in presence of other cations in the human blood serum is an important and interesting discovery. The blood serum electrolyte content is as follows: Cl (97-107 mM), Na (132-144 mM), K (3.6-4.8 mM), Ca (2.0-2.7 mM), Mg (0.7-1.2 mM), Al (17-32.6 µM), Br (0.09 µM), Cu (12-22.5 µM), F (5.3-23.7 µM), I (0.4-0.7 µM), Fe (5.7-31.7 µM), Pb (0.1-0.4 µM), Mn (1.5-3.5 µM), Sn (0.3-8 µM), Zn (0.9-3.7 µM). The highlight of this invention is the ability of crown ether ionophore to select potassium and sense accurately even in low concentration range of blood serum. Most interestingly, this ionophore is specifically selective to potassium even in the presence of 36% higher sodium concentration. The performance of the biosensor is validated as it obeys Nernst law and gives a slope value of 59.2 mV/decade for the plot of potential vs. concentration.

BRIEF DESCRIPTION OF THE DRAWINGS

FIG. 5 Study of pH distribution of blood serum samples.

FIG. 6 ISFET response characteristics at very low KCl concentrations (a) without and (b) with crown ether layer on the gate.

FIG. 7 Semi-logarithmic plots for the ISFET characteristics.

FIG. 8 Distribution of ISFET potential with number of patients.

FIG. 9 Distribution of potassium ion concentration with number of patients.

FIG. 10 Plots of potential versus NaCl concentration for ISFETs without and with crown ether layer on the gate.

DETAILED DESCRIPTION OF INVENTION

Figure 2:
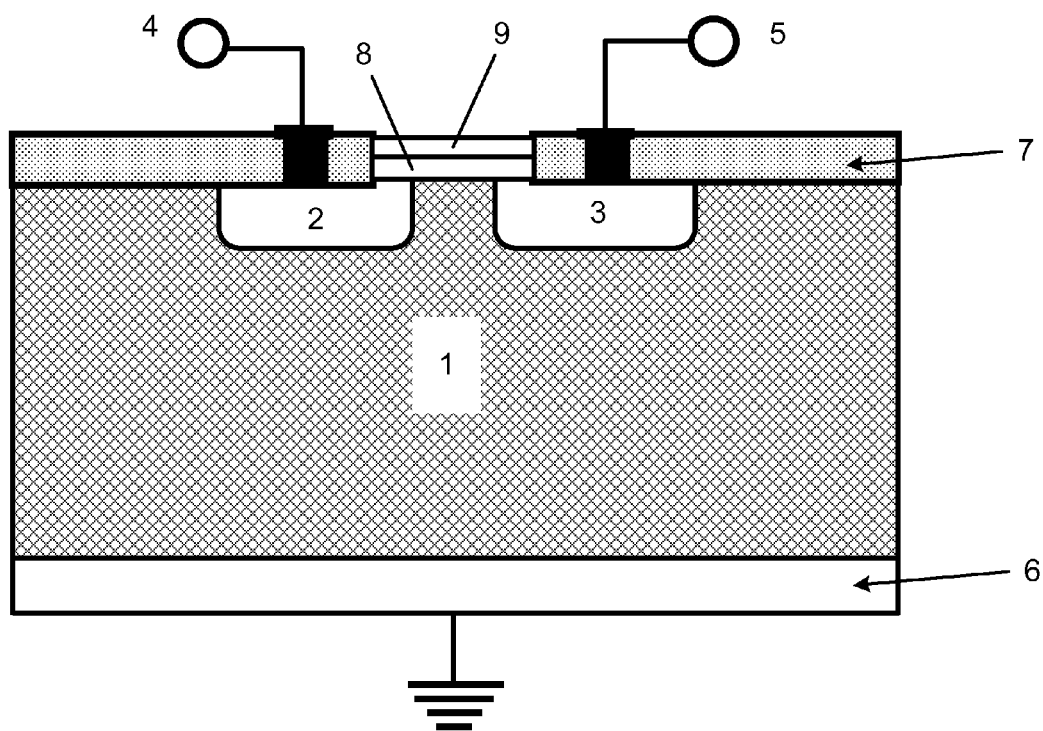
FIG. 2 Schematic cross-section of potassium ISFET.

Accordingly, the present invention provides an improved and advanced version of the biosensor to determine the low concentration range of Potassium (3.6-4.8 mM or 151.22-205.4 mg/litre)) in human blood serum. The components of the biosensor as shown in FIG. 2 and described herein are as follows:

1: P-substrate: The starting material on which the ISFET is fabricated. Here P-type Czochralski silicon wafer of resistivity 15-20 ohm-cm ($7.4 \times 10^{14}$ $cm^{-3}$) and orientation <100> has been used.

2, 3: $N^+$ source and drain regions: Heavily phosphorous diffused regions in P-substrate. The source is so named because it is the source of the charge carriers (electrons for N-channel, holes for P-channel) that flow through the channel; similarly, the drain is where the charge carriers leave the channel.

4, 5: Terminal connections for source and drain: These are wires or leads for taking connections from source and drain regions of the ISFET.

6: Substrate connection which is grounded: Wire or lead from the P-substrate that is kept at ground potential during ISFET operation.

7: Field oxide: Thick oxide layer in a MOS device. It is formed to passivate and protect semiconductor surface outside of active device area. Actually, it is a part of ISFET but does not participate in device operation 8: $SiO_2+Si_3N_4$ gate dielectric: An insulator made of two layers, silicon dioxide and silicon nitride, used between the gate and substrate of ISFET.

9: Crown ether layer: Potassium-ion selective layer applied on the gate.

Components 1 to 8 comprise the ISFET. Component 9, the crown ether coating on the gate, provides selectivity to the sensor for potassium ions. On trapping $K^+$ ions by the crown ether layer, the gate-source potential increases. The change in gate-source potential as a function of potassium ion concentration gives the calibration characteristic of the sensor.

As the blood serum samples had a narrow spread of pH range, influence of pH variations on the measurements is insignificant. Cross-sensitivity of crown ether ISFET towards sodium ions has also been investigated and found to have negligible effect. As the sensing material or ionophore, dibenzo-18-crown-6 is readily amenable to chemical modification as it attaches potassium via ion-pair formation and exhibits selective host-guest chemistry. The response time of biosensor is 30-60 seconds and the ionophore is stable for a cycle life of one week. The shelf life is robust and can be idle even for months and reactivated by immersing in a diluted solution of KCl. The most important requirements of an ion sensor are fulfilled by our biosensor as follows: (1) Small ~5 ml of sample volume, 12/4800µ dimensions (ISFET) required for guaranteed analysis; (2) High selectivity in presence of other ions that may be found in biological samples; (3) High linearity of sensors response in a blood serum concentration range.

In an embodiment of present invention, a device for measuring the concentration of ions in human blood serum characterized in having a coating of dibenzo-18-crown-6 dissolved in chloroform.

In another embodiment of present invention, dibenzo-18-crown-6 is used as ionophore to enable the specific selectivity of potassium in blood serum.

Figure 1:
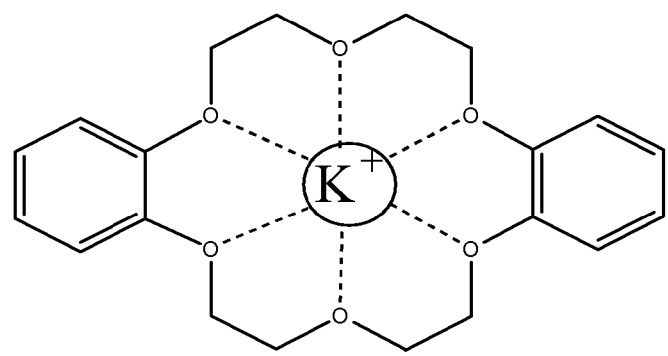
FIG. 1 Binding of the potassium ion within the crown ether molecular structure.

In yet another embodiment of present invention, dibenzo-18-crown-6 acts as host with 2.6-3.2 A° cavity size which fits the exact size of potassium ion of 2.66 A° (guest) and makes it an excellent choice to be a sensing material for potassium ions (FIG. 1).

In another embodiment of present invention, the amount of crown and chloroform used for the coating was 200-500 mg and 0.25-0.75 ml respectively.

In yet another embodiment of present invention, crown ether has been deposited on the ISFET gate by dissolving the crown ether in chloroform and placing a drop over the ISFET gate.

In still another embodiment of present invention, each 1 ml of human blood serum was diluted to 50 times.

In an embodiment of present invention, the effect of pH in blood serum samples was proved to be nil. These diluted samples showed a constant pH ~7.0-7.1, confirming the maintenance of pH within close tolerance by the human body; therefore any errors due to pH variation amongst the samples were eliminated (FIG. 5).

In another embodiment of present invention, ISFET response characteristics at very low KCl concentrations (blood serum range) (a) without and (b) with crown ether layer on the gate and the derived plots show the gate with crown ether fare 2.16 times higher sensitive than the gate without crown ether (FIGS. 6 and 7).

In yet another embodiment of present invention, blood serum (fresh or stored) samples were tested for potassium concentration using ISFET-crown ether gate and the out potential was recorded. (FIG. 8)

In another embodiment of the present invention, chloroform is used for dissolving dibenzo-18-crown-6.

The invention is described in detail with reference to the examples given below which are provided to illustrate the invention and therefore, should not be construed to limit the scope of the invention.

EXAMPLE 1

Fabrication and Package of ISFET Device

The device has been fabricated on P-type Czochralski silicon wafers of resistivity 15-20 ohm-cm ($7.4\times10^{14}$ cm$^{-3}$) and orientation <100>. Fabrication technology of the ISFET, based on the NMOSFET technology comprised the following processing steps: (i) Field oxidation (1100° C., 30 min. dry $O_2$+120 min. wet $O_2$+30 min. dry $O_2$) giving oxide thickness=0.9 µm. (ii) First photolithography for source/drain N$^+$ diffusion, and oxide etching. (iii) Phosphorous diffusion (1050° C., 30 min.): Sheet resistance<3 ohms/square cm. (iv) Second photolithography for gate window, and oxide etching. (v) Gate oxidation (trichloroethylene ambient), 1000° C., 120 min., dry $O_2$, oxygen flow rate 2 litre/min, a little TCE vapour was carried down the tube by a slow bleed of $N_2$ through TCE bubbler at 25° C., $t_{ox}$=140 nm. (vi) Nitridation (LPCVD), 780° C., 25 min, initial pressure=0.02 torr, deposition pressure of dichlorosilane and ammonia gas mixture=0.2 torr, dichlorosilane=20 cc, ammonia 200 cc, gas ratio=1:10, $t_{Nitride}$=100 nm; annealed at 900° C. for 30 min in $N_2$. (vii) Third photolithography for contact holes, and oxide etching. (viii) Sputtering of chromium (50 nm) and gold (500 nm). (ix) Fourth photolithography for metal pattern delineation, and metal etching. (x) Metal sintering, (xi) Wafer scribing, and chip sorting and mounting on ceramic substrate. (xii) Wire bonding. (xiii) Protecting the metal pads and wires by insulating epoxy (Epotek H 70E/H74, cured at 120° C., 30 min.) with soldering pads protected by RTV compound. The gate region has been left exposed.

EXAMPLE 2

Deposition of Crown Ether on the Gate Region of ISFET

Crown ether has been deposited on the ISFET gate by dissolving the crown ether in few drops of chloroform to form a paste. Usually, few micrograms of the ionophore were sufficient to coat the gate ISFET.

EXAMPLE 3

Optimization of Coating on Gate 200 mg of crown dissolved in chloroform solvent forms a monolayer of the coating on the surface of the gate. On exposure to air at room temperature, chloroform evaporates at once and leaves behind the ionophore.

EXAMPLE 4

Measurement Procedure

Measurements have been carried out using an in-house assembled signal conditioning circuit for direct reading of pH. An Ag/AgCl reference electrode has been used. This circuit gives an output voltage equal to the pH of the solution in which the ISFET is immersed. The circuit including the ISFET has an overall voltage gain of 20. The measurements have been performed before and after crown ether layer deposition.

Device operation: On trapping K$^+$ ions by the crown ether layer, the gate-source potential increases. The change in gate-source potential as a function of potassium ion concentration gives the calibration characteristic of the sensor.

The following steps are involved in measuring the potassium ion concentration:
a) dipping the ISFET gate in the serum
   ISFET was dipped in 50 ml of standard solutions and serum for measuring the potential.
b) reading the potential
   Potential was read for each standard and serum sample. Standard plot—potential difference/concentration was drawn for standard samples.

c) matching the read potential with that of the standard values: Potassium concentration in the serum sample was obtained from the standard graph

EXAMPLE 5

Characterization and Standardization and Calibration of ISFET

Figure 3:
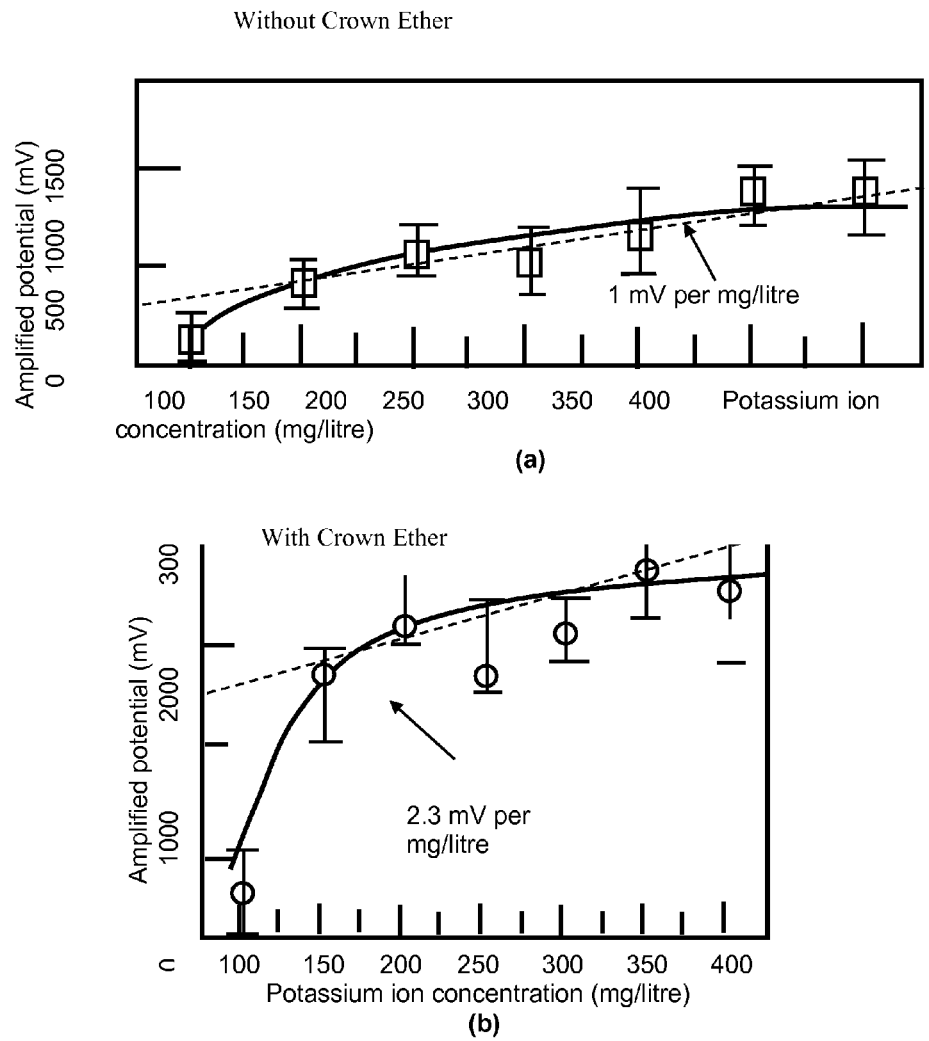
FIG. 3. ISFET response characteristics (a) without and (b) with crown ether layer on the gate; measurements have been carried out in standard KCl solutions with concentrations in human blood serum range.
Figure 4:
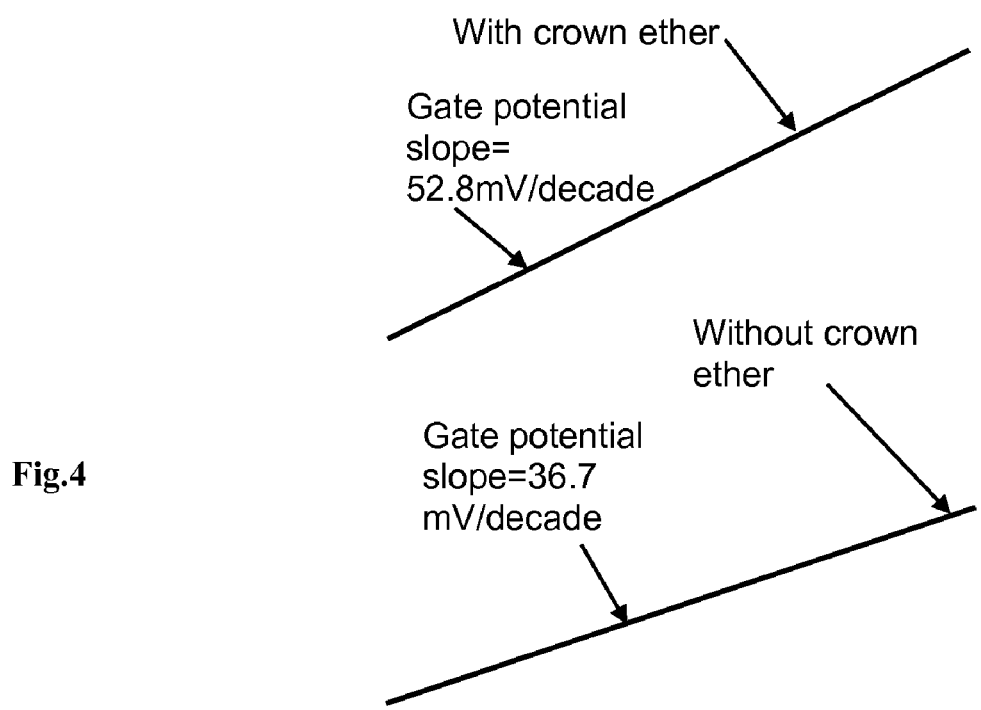
FIG. 4 Plots of the potentials relative to logarithm of potassium ion concentration obtained from ISFET characteristics.

Characterization of ISFET was done with respect to KCl concentration from 100 to 400 mg/litre which is in the range of interest for the human blood serum analysis. Standardization of ISFET with KCl solutions with and without crown ether was studied. (FIG. 3). The blood serum samples were prepared for measurement with ISFET by diluting 1 ml each of human blood serum samples to 50 ml because the 1 ml solution was insufficient for dipping ISFET along with the reference electrode.

The measurement of potentials related to potassium ion concentration in different blood serum samples were done with and without crown ether on the ISFET gate.

The ISFET calibration using atomic absorption spectroscopy for standard KCl solutions and diluted human blood serum samples.

Advantages:

The biosensor can detect potassium ions in human blood serum with high specificity even in 50 times diluted blood.

The sensitivity and specificity of the biosensor is due to coating of Crown ether, Di benzo 18-crown 6-ether over the dual dielectric silicon dioxide Silicon nitride gate.

It is easy to prepare, assemble and economically viable.

The DB18C6 ionophore could be used in the disposable mode if it is made in the form of strip that has the dimensions of the ISFET gate.

The preparative method does not involve complicated procedure and is economically very promising because each fresh monolayer requires less than 500 microgram of the crown ether.

The response time of ionophore was within a minute.

The shelf life of the electrode either on use or idle, was found to be a three months period.

The electrode surface can be re-coated and used.

The invention claimed is:

1. A device for measuring the concentration of ions in human blood serum, said device comprising:
    a) an ISFET (Ion Selective Field Effect Transistor) as a working electrode wherein the ISFET includes a P substrate, $N^+$ source and drain regions diffused in the P substrate, terminal connections embedded on the P substrate for the source and the drain regions for taking connections from the source and the drain regions of the ISFET, a substrate connection which is grounded, a field oxide, a silicon dioxide/silicon nitride dual dielectric gate and a thin mono-layer consisting of dibenzo-18-crown-6 as an ionophore applied to the gate of the ISFET wherein the ionophore on the gate consists of the monolayer of the dibenzo-18-crown-6; and
    b) a Ag/AgCl as a reference electrode.

2. The device according to claim 1 wherein, a response time of the device with the ionophore is less than a minute and a shelf life of the working electrode either on use or idle is at least three months.

3. The device according to claim 1, wherein the said dibenzo-18-crown-6 is dissolved in chloroform and coated above onto the silicon dioxide/silicon nitride gate as a monolayer.

4. The device according to claim 3, wherein, the said dibenzo-18-crown-6 and chloroform are mixed in the ratio of 200 mg-500 mg:0.5 ml-0.75 ml, respectively.

5. The device according to claim 4, wherein the amount of chloroform used in the mixture ranges from 0.25-0.75 ml.

6. The device according to claim 4, wherein the amount of chloroform in the mixture is preferably 0.5 ml.

7. The device according to claim 4, wherein the concentration of dibenzo-18-crown-6 in the mixture ranges from 200 mg to 500 mg.

8. The device according to claim 4, wherein the concentration of dibenzo-18-crown-6 in the mixture is preferably 200 mg.

9. The device according to claim 4, wherein a cavity size of dibenzo-18-crown-6 is selected from the range of 2.6-3.2 A°.

10. A method of measuring the concentration of ions in human blood serum using the device according to claim 1, comprising
    a. dipping the ISFET gate in the serum;
    b. reading a potential generated in step a) of the ISFET gate;
    c. matching the read potential of step b) with that of standard values.

11. The method according to claim 10, comprising measuring potassium ion concentration in human blood.

12. The method according to claim 10, comprising measuring concentration of ions from fresh or stored blood.

13. The method according to claim 10, comprising measuring a concentration of ions with high specificity in blood diluted from 1:5 to 1:50 times.

* * * * *